United States Patent
Osby

(10) Patent No.: US 11,058,203 B2
(45) Date of Patent: Jul. 13, 2021

(54) NAIL PRODUCTS, METHODS OF USE AND KITS

(71) Applicant: LUCYPOP, Inc., Detroit, MI (US)

(72) Inventor: Tonia Osby, Detroit, MI (US)

( * ) Notice: Subject to any disclaimer, the term of this patent is extended or adjusted under 35 U.S.C. 154(b) by 0 days.

(21) Appl. No.: 16/911,969

(22) Filed: Jun. 25, 2020

(65) Prior Publication Data

US 2020/0405033 A1 Dec. 31, 2020

Related U.S. Application Data

(60) Provisional application No. 62/866,049, filed on Jun. 25, 2019.

(51) Int. Cl.
| | |
|---|---|
| *A45D 29/00* | (2006.01) |
| *A61K 8/65* | (2006.01) |
| *A61K 8/97* | (2017.01) |
| *A45D 29/04* | (2006.01) |
| *A61K 45/06* | (2006.01) |

(52) U.S. Cl.
CPC .......... *A45D 29/001* (2013.01); *A45D 29/04* (2013.01); *A61K 8/65* (2013.01); *A61K 8/97* (2013.01); *A45D 2029/045* (2013.01); *A61K 45/06* (2013.01); *A61K 2800/10* (2013.01); *A61K 2800/805* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 2,096,389 | A | 10/1937 | Bode |
| 2,323,595 | A | 7/1943 | Hanisch |
| 2,864,384 | A | 12/1958 | Walter |
| 3,421,521 | A | 1/1969 | Rich, Jr. |
| 3,682,738 | A | 8/1972 | Smith |
| 3,856,026 | A | 12/1974 | Gaydos |
| 4,058,442 | A | 11/1977 | Lee, Jr. et al. |
| 4,094,316 | A | 6/1978 | Nathanson |
| 4,142,929 | A | 3/1979 | Otomine et al. |
| 4,161,176 | A | 7/1979 | Harris, II et al. |
| 4,196,741 | A | 4/1980 | Minghenelli |

(Continued)

FOREIGN PATENT DOCUMENTS

| | | |
|---|---|---|
| CA | 1036359 A | 8/1978 |
| CA | 1321939 C | 9/1993 |

(Continued)

OTHER PUBLICATIONS

Flock University 1st Edition—Flock Basics; https://www.spectrocoating.com/single-post/2015/01/28/Flock-University-1st-Edition-Flock-Basics. Published Jan. 28, 2015, accessed Jun. 23, 2020.

(Continued)

*Primary Examiner* — Nicole P Babson
(74) *Attorney, Agent, or Firm* — Frost Brown Todd LLC

(57) ABSTRACT

Nail products, methods and kits for enhancing nails are disclosed. A tacky substance is applied to a nail followed by a nonwoven substrate. The nonwoven substrate is removed from the nail leaving a fiber residue on the nail. A nail coating such as nail polish is applied to the nail over the fiber residue. If any gaps between fibers in the fiber residue remain after the nail coating is applied, a further nail coating may be applied. A top coat may then be applied to provide for a final finish on the nail.

20 Claims, 9 Drawing Sheets

(56) References Cited

U.S. PATENT DOCUMENTS

| | | |
|---|---|---|
| 4,267,852 A | 5/1981 | Hullinger |
| 4,407,310 A | 10/1983 | Jadow |
| 4,421,809 A | 12/1983 | Bish |
| 4,552,160 A | 11/1985 | Griggs |
| 4,554,935 A | 11/1985 | Hokama |
| 4,594,276 A | 6/1986 | Relyea |
| 4,626,428 A | 12/1986 | Weisberg et al. |
| 4,627,453 A | 12/1986 | Isler |
| 4,641,669 A | 2/1987 | Kimble |
| 4,646,765 A | 3/1987 | Cooper et al. |
| 4,669,491 A | 6/1987 | Weisberg et al. |
| 4,671,305 A | 6/1987 | Mann |
| 4,751,935 A | 6/1988 | Mast et al. |
| 4,860,774 A | 8/1989 | Becker |
| 4,873,077 A | 10/1989 | Thompson et al. |
| 4,903,840 A | 2/1990 | So |
| 4,943,462 A | 7/1990 | Komerska et al. |
| 4,992,490 A | 12/1991 | Childress et al. |
| 5,091,240 A | 2/1992 | Kajander et al. |
| 5,209,250 A | 5/1993 | Taeckens |
| 5,209,877 A | 5/1993 | Frances et al. |
| 5,370,866 A | 12/1994 | Frankfurt et al. |
| 5,474,842 A | 12/1995 | Hoiness |
| 5,632,973 A | 5/1997 | Keller |
| 5,770,184 A | 6/1998 | Keller |
| 6,075,882 A | 6/2000 | Mullins et al. |
| RE38,246 E | 9/2003 | Leonard et al. |
| 6,613,339 B1 | 9/2003 | Yamada et al. |
| 6,631,723 B1 | 10/2003 | Mullin |
| 6,647,549 B2 | 11/2003 | McDevitt et al. |
| 6,863,076 B2 | 3/2005 | Russell |
| 7,870,633 B2 | 1/2011 | Thiebaut |
| 7,927,691 B2 | 4/2011 | Khan et al. |
| 8,474,464 B2 | 7/2013 | Smith |
| 2002/0017310 A1 | 2/2002 | Gruenbacher et al. |
| 2004/0191192 A1 | 9/2004 | Blankenbeckler et al. |
| 2011/0028878 A1 | 2/2011 | Smith et al. |
| 2014/0007894 A1 | 1/2014 | Gagnon |
| 2014/0053863 A1 | 2/2014 | Chudzik |
| 2015/0013709 A1 | 1/2015 | Scheurn et al. |

FOREIGN PATENT DOCUMENTS

| | | |
|---|---|---|
| CN | 1116842 C | 7/1998 |
| CN | 203873210 U | 10/2014 |
| EP | 1358818 A1 | 11/2003 |
| EP | 2457460 A1 | 5/2012 |
| FR | 2415439 A1 | 8/1979 |
| JP | 4851594 B2 | 1/2012 |
| JP | 2016175883 A | 10/2016 |
| JP | 6113512 B2 | 4/2017 |
| KR | 101337224 B1 | 12/2013 |
| KR | 101906154 B1 | 10/2018 |
| SE | 8400416 L | 8/1984 |

OTHER PUBLICATIONS

Flock University 2$^{nd}$ Edition—Adhesives; https://www.spectrocoating.com/single-post/2015/01/28/Flock-University-2nd-Edition---Adhesives. Published Jan. 28, 2015, accesses Jun. 23, 2020.

Flock University 3$^{rd}$ Edition—Our process; https://www.spectrocoating.com/single-post/2015/02/05/Flock-University-3rd-Edition-Our-Process. Published Feb. 5, 2015, accessed Jun. 23, 2020.

Flock University 4$^{th}$ Edition—Flock and Tech; https://www.spectrocoating.com/single-post/2018/06/14/Flock-University-4th-Edition---Flock-and-Tech. Published Jun. 14, 2018, accessed Jun. 23, 2020.

Joshi, M., et al. "Antimicrobial textiles for health and hygiene applications based on eco-friendly natural products." *Medical and Healthcare Textiles*. Woodhead Publishing, 2010. 84-92.

International Search Report and Written Opinion dated Sep. 4, 2020 for International Application No. PCT/US2020/039573, 13 pages.

NAIL PRODUCTS, METHODS OF USE AND KITS

PRIORITY

This application claims priority to U.S. Provisional Patent Application Ser. No. 62/866,049, filed on Jun. 25, 2019, and entitled, "Nail Enhancements," the disclosure of which is incorporated by reference herein.

TECHNICAL FIELD

The present disclosure relates to the field of cosmetology and more particularly, relates to products, kits and methods that may protect the integrity and health of nails, as well as provide for durability of nail coatings, including nail polish.

BACKGROUND

Consumers may use nail coatings to cosmetically enhance the appearance of their nails, repair their nails and/or to protect their nails (individually and collectively referred to herein as "enhance nails" or apply "nail enhancement(s)") from abuses found in their everyday environments. Consumers may also desire a durable nail polish. Lack of durability is often evidenced by unsightly chipping or peeling of nail polish soon after the original coating has been applied, requiring at least in part, a reapplication of the coating in an attempt to recreate the aesthetic appearance or the therapeutic benefits of the original nail coating. A number of attempts have been made to provide for nail coatings that are purported to be either decorative, long-lasting or both decorative and long-lasting as described below.

Flocking has been used as a nail embellishment. A well-known example of a flocked surface is the ubiquitous engagement ring box, which has a velvety look and feel as a result of the flocking applied thereto. U.S. Pat. No. 3,856,026, which is entitled, "Application of Flock to the Body for Cosmetic Purposes" (hereinafter, "Cochran"), describes applying flock to fingernails, toenails, eyelids, eyebrows, eyelashes and other portions of the body for cosmetic purposes. Cochran describes flock as a very short or pulverized fiber that may be applied by blowing or shaking, onto a surface of the body. In one disclosed method, flock is applied directly to an adhesive-coated nail and excess flock removed. In another disclosed method, a sheet of film of a plastic material, having an adhesive backing, is coated with an adhesive base and the flock applied to the adhesive base, after which portions of the sheet or film are removed for application to the fingernail or other body part. Korean Pat. No. KR 101337224 describes a flocking nail sticker that may comprise several layers including a picture or pattern of flock on PET fabric.

Artificial hair, fur or fabrics have also been used as nail embellishments. For example, U.S. Pat. No. 6,631,723, which is entitled, "Artificial Nails with Three Dimensional Features" (hereinafter, "Mullin"), describes artificial nails with 3-D representations on their surface of any known or imagined person, place or thing. Mullin indicates that the 3-D features may be made from artificial hair, fur or fabric and may be removably attached to the artificial nails. U.S. Pat. No. 4,627,453, which is entitled, "Artificial Fingernails and Method of Application," describes an artificial fingernail that is formed from layers of organic fabric, such as flax, linen and silk, applied layer by layer over a wearer's natural nail with an adhesive, and hardened with a hardening solution. U.S. Pat. No. 4,627,453, which is entitled, "Artificial Fingernails and Method of Application," describes artificial fingernails that are formed from layers of organic fabric, such as flax, linen and silk, applied layer by layer over a wearer's natural nail with an adhesive, and hardened with a hardening solution. U.S. Pat. No. 4,641,669, which is entitled, "Method for Reinforcing and Hardening Human Nails" (hereinafter, "Kimble"), provides a nail treating process which includes applying to the natural nail surface a patch cut from a thin mat of non-heat sealed random cellulose fibers, such as may be formed of hemp and other natural cellulose fibers, followed by saturation of the in-place patch with a cyanoacrylate glue. Kimble discloses that individual fibers in the mat are thereby bonded to one another and to the nail surface, thus, forming a protective nail coating. Japanese Pat. No. 6113512, which is entitled, "Silk Wrap or Fiber Wrap for Nail Repair," describes nail repair and reinforcement methods including the application of silk or fiberglass wraps on the surface of the nail for nail repair and extension. U.S. Pat. No. 4,860,774, which is entitled, "Fingernail Reinforcement Material and Method," describes a fingernail reinforcement extension material that is formed of a woven fiberglass fabric having a vertical and horizontal cross-thread count in the range of 25 to 55 threads per inch.

Powders have been used to reinforce nails. U.S. Pat. No. 4,669,491, which is entitled, "Compositions and Process for Applying Protective Covering and Extensions to Fingernails" (hereinafter, "Weisberg"), describes problems with nail sculpting, noting that it requires a great deal of training and skill. Moreover, Weisberg indicates that the thick, tough acrylic nail becomes permanently attached to the point where it is applied through the application of a series of chemicals including bromide, cyanoacrylate ester, or methacrylic acid, a blend of mono-, di- and trimethacrylate esters and N, N, dimethyl-para-toluidine, which is capable of inducing the decomposition of benzoyl peroxide at room temperature. Weisberg further describes an alternative to nail dipping by comprising a 5-step process that involves applying a layers of chemicals to the nail, including a liquid methacrylic monomer blend, a powder comprising polymethacrylic ester, a second layer of a liquid methacrylate monomer blend, curing the coating, and then adding a water free solution of biocide selected from the group of n-alkyldimethylbenzylammonium chloride, cetyl pyridinium bromide, 5-methyl-2-isopropyl-cyclohexanol, 2-bornanone, cineole, safrole, bornyl chloride, 2-phenoxyethanol, benzyl alcohol, ethanol, thymol, chlorothymol, benzoic acid, p-hydroxybenzoate alkyl esters, 4- and 6-phenyl-2-chloro-phenol, carvacrol and hexachlorophene.

Fibers suspended in liquid have been used to reinforce nails. U.S. Pat. No. 4,669,491, which is entitled, "Process for Enhancing and Strengthening the Growth of Nails" (hereinafter, "Hullinger"), describes issues with prior art treatments involving applying false fingernails, i.e. tips, and indicates that such false acrylic nails tend to deteriorate the fingernails, i.e., the false acrylic nails do not let the underlying natural nails "breathe." Hullinger purports to overcome the prior art issues by providing improved nail hardening, which may include application to the tops and undersides of nails of a liquid composition containing a fibrous material, described as microscopic fibers, such as nylon fibers, followed by applicant of a sealer and hardener, as a preparation for adhering nail polish to the nails. U.S. Pat. No. 4,873,077, which is entitled, "Fingernail Reinforcement Material and Method," purports to add strength and protection to the nails by applying an improved nail hardener that comprises a nitrocellulose-based nail lacquer and fiber glass that is 10 microns in diameter by 800 microns long, which may be followed with final coats of nail polish. U.S. Pat. No. 4,646,765, which is entitled, "Nail Compositions Containing Cyanoacrylate and Graphite" (hereinafter, "Cooper"), describes a composition for adhering to human nails that includes a mixture of a cyanoacrylate compound and/or graphite fibers. Cooper indicates that the composition can take the form of either an artificial nail extender or a nail coating and comprises graphite fibers and cyanoacrylate in the form of a base material, that is applied to the nail and hardened by applying a hardening accelerator containing a mixture of trichlorotrifluoroethane and N,N-dimethyl-P-toluidine. U.S. Pat. No. 5,370,866, which is entitled, "Colorless or Colored Nail Polish Containing Aramide Fibers," describes colorless or colored nail polish that contains, in a nail polish solvent system, a film-forming substance, a resin, a plasticizer and 0.01 to 0.5 wt. % aramide fibers (poly [paraphenylene terephthalamide]).

A need remains for nail products that protect and strengthen the nail as well as provide for improved nail polish durability. Such nail products may be gentle to the nail, including the nail plate and nail bed, and may be easily applied and removed by a consumer as well as a nail technician. Such nail products may not require specialized equipment such as UV/UVA curing lights. Such nail products may not require harsh abrasion (manual or mechanical) to remove them. Such nail products may not require use of harsh chemicals during application or removal. Such nail products should be compatible with a wide variety of commercially available nail coatings. Such nail products should be relatively less expensive and require less time to complete than using products and methods requiring multiple steps and/or use of a variety of chemicals, tools and/or equipment. Such nail products may provide for a smooth appearance that is also smooth to the touch and retains its glossy appearance with normal wear. While a variety of compositions and methods for enhancing nails have been made and used, it is believed that no one prior to the inventor has made or used an invention as described herein.

BRIEF SUMMARY

The present disclosure is directed to nail products, kits and methods of use, which address and overcome issues with known nail products, while providing one or more of the aforementioned consumer benefits as well others that are described herein below.

The present disclosure describes a method of enhancing a nail comprises: (a) applying a tacky substance to the nail; (b) supplying a nonwoven substrate having a first side and a second side disposed opposite to the first side; (c) adhering the first side of the nonwoven substrate to the tacky substance disposed on the nail; (d) removing the nonwoven material from the tacky substance, leaving a first fiber residue disposed on the tacky substance; and (e) applying a first nail coating over the first fiber residue; wherein the first nail coating adheres to the fibrous residue.

The present disclosure further describes a nail product comprising: (a) a tacky substance that is configured to be coated on a nail; (b) a nonwoven substrate that is folded over onto itself and sealed at two overlapping edges to form a pocket with one open end, wherein the nonwoven substrate is configured to: i. receive one or more fingers or toes into an interior of the nonwoven substrate through the open end of the pocket; and ii. leave a fiber residue on at least one nail disposed on at least one or more of the fingers or toes, wherein the at least one nail is coated with the tacky substance.

The present disclosure further describes a kit for enhancing nails, the kit comprising a package that contains (a) a plurality of nonwoven substrates; (b) a buffer block; (c) a container of base coat; (d) a container of nail coating; and (e) a container of top coat.

BRIEF DESCRIPTION OF THE DRAWINGS

It is believed the present invention will be better understood from the following description of certain examples taken in conjunction with the accompanying drawing.

Figure 1:
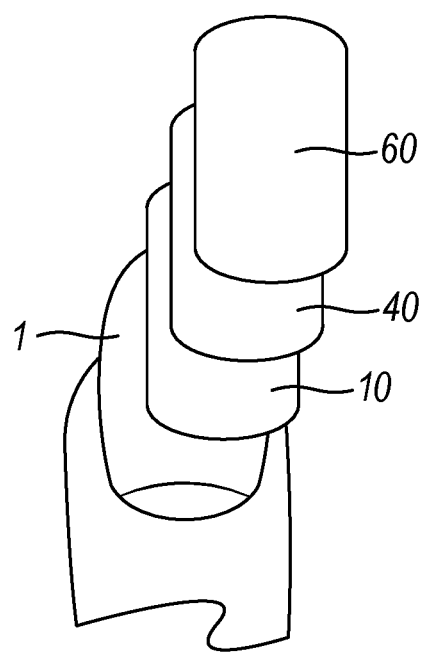
FIG. 1 depicts a graphical representation of layers of nail product applied to a nail as is known in the art.

The drawings are not intended to be limiting in any way, and it is contemplated that various embodiments of the invention may be carried out in a variety of other ways, including those not necessarily depicted in the drawing. The accompanying drawing that is incorporated in and forms a part of the specification illustrates several aspects of the present invention, and together with the description serves to explain the principles of the invention.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

All references, including patent applications, patent publications and non-patent literature, that are referred to in the present specification are incorporated by reference herein, unless it is expressly indicated that they are not incorporated by reference herein.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9 and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made. The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, "nail" means a toenail, fingernail or thumbnail of a human or animal.

As used herein, "nail coating" means all pigmented, clear and translucent nail coatings. Exemplary nail coatings may include those that are matte, metallic, chromic, pearlescent, contain glitter, are in gel form, are in crème form and so on.

"Fiber" as used herein means continuous fibers, which are sometimes referred to in the art as "substantially continuous filaments," "filaments," or "yarn," or staple fibers (noting that silk is a natural fiber that may not have a staple form), Fibers may be hydrophobic or hydrophilic depending upon the formulations of the tacky substance and nail coatings as described herein below. Exemplary fibers of use with tacky substances and nail coatings are hydrophobic may be hydrophobic fibers.

"Monocomponent fiber" as used herein, refers to a fiber formed from using one or more extruders from only one polymer; this is not meant to exclude fibers formed from one polymer to which small amounts of additives have been added. Additives may be added to the polymer for the purposes of providing the resulting fiber with coloration, antistatic properties, lubrication, hydrophilicity, and/or other properties. Monocomponent fibers may be multifilament or monofilament fibers.

"Multicomponent fiber" as used herein, refers to a fiber formed from two or more different polymers that are extruded from separate extruders and spun together to form one fiber.

"Bicomponent fibers" are one type of multicomponent fiber, and are formed from two different polymers. Bicomponent fibers may sometimes be referred to in the art as "conjugate fibers." Bicomponent fibers may be comprised of polymers that are substantially continuously positioned in distinct zones, both across the cross-section of the bicomponent fibers and along their length. Non-limiting examples of such bicomponent fibers include, but are not limited to: sheath/core arrangements, wherein one polymer is surrounded by another; side-by-side arrangements; segmented pie arrangements; or even "islands-in-the-sea" arrangements. Each of the aforementioned polymer arrangements is known in the art of multicomponent (including bicomponent) fibers. Bicomponent fibers can be splittable fibers. Such fibers are capable of being split lengthwise before or during processing into multiple fibers with each of the multiple fibers having a smaller cross-sectional dimension than that of the original bicomponent fiber. Splittable fibers may provide softer fabrics due to their reduced cross-sectional dimensions. "Biconstituent fibers" as used herein, refers to fibers which have been formed from at least two starting polymers extruded as a blend from the same extruder. Biconstituent fibers may have the various polymer components arranged in relatively constantly positioned distinct zones across the cross-sectional area of the fiber, and the various polymers are usually not continuous along the entire length of the fiber. In the alternative, biconstituent fibers may comprise a blend, that may be homogeneous or otherwise, of the at least two starting polymers. For example, a bicomponent fiber may be formed from starting polymers which differ only in molecular weight. Biconstituent fibers may form fibrils, which may begin and end at random along the length of the fiber. Biconstituent fibers may sometimes be referred to as multiconstituent fibers.

As used herein, "nonwoven substrate" means a nonwoven material made from fibers that are bonded together by chemical, mechanical, heat and/or solvent treatment as is known in the art. Non-limiting examples of useful nonwovens may be selected from the group of spunlace nonwovens, heat-bonded nonwovens, spunbond nonwovens and meltblown nonwovens.

Referring to FIG. 1, a typical at-home or salon nail polishing process may comprise applying at least three nail products—base coat (10), nail polish (40) and top coat (60). Typically, a base coat (10) is applied directly to a prepared (e.g., cleaned and shaped) nail (1). After the base coat (10) has dried sufficiently to be tacky, nail polish (40) is applied over the base coat (10). In some instances, a second coating of nail polish may be applied (not shown). After the top layer of nail polish (40) has dried, a top coat (60) is applied over the nail polish (40). After the top coat (60) has dried, the nail polishing process may be concluded or further embellishments applied to the nail. The inventor has surprisingly found that the nail products, kits and methods described herein, overcome issues with known nail products and methods of use, while providing one or more of the aforementioned consumer benefits as well others that are described herein below.

Notably, the nail products, kits and methods as described herein may be counterintuitive to one of ordinary skill in the art, since they surprisingly involve leaving a fiber residue on a surface of a nail, prior to adding a nail coating thereto (e.g., nail polish) to provide for results that are expected by the consumer—a finished nail that appears smooth and glossy and that is also smooth to the touch. To wit, to the best of inventor's knowledge, it is common in nail technician training materials, advertisements for salon nail treatments, nail product descriptions and in professional online forums, to find teachings away from painting nails that have any fiber residue deposited thereon. For example, it is noted that lint and fluff, which can stick to the nailbed when prepping a nail for application of nail polish, is to be avoided. See: *Tips and Tricks for the Working Nail Technician*, published Mar. 4, 2019 at: https://www.hairandbeautyjobs.com/article/nail-technician-profile/tips-and-tricks-for-the-working-nail-technician/. In a further example, Advance Beauty College's CND Spa Manicure is advertised as a "Signature Service" that comprises using Scrub Fresh (alcohol base) and a lint-free wipe to remove oil from nails and clean underneath the nails, prior to adding a base coat of Vinylux. See: https://www.nailsmag.com/381820/signature-services-advance-beauty-colleges-cnd-spa-manicure, published on Jan. 15, 2016. In a further example, it is taught that a nail plate is prepared for receiving a nail enhancement by, among other steps, removing all residues and sanitizing the surface by scrubbing the nail plate with a lint-free pad. See: *The Encyclopedia of Nails, $2^{nd}$*, Habia City & Guilds, 2006, at p. 210, and *Milady Standard Cosmetology*, Cengage Learning, 2014, at p. 978, 983 and 989. In a further example, a discussion on the Salon Geek web forum informs others of where the best lint free wipes may be purchased and that they are to be used when applying top coats to nails. See: https://www.salongeek.com/threads/best-lint-free-wipe-i-have-found-yet.182096/, published on May 26, 2012 and https://www.nailsmag.com/378129/how-to-apply-and-remove-cnd-shellac-luxe, published on Jun. 22, 2020 (a search of "lint free" generates 3,475 "hits"). In a further example, a Google search of "lint free nail products" on Jun. 3, 2020, generates about 4,920,000 results. The present disclosure is directed to nail products, methods of use and kits that address and overcome issues with known nail products and methods of use, by intentionally depositing fiber residue on the nail prior to polishing the nail, thereby providing one or more of the aforementioned consumer benefits as well others that are described herein below.

Nail products in accordance with the present disclosure may be applied directly to the surface of a nail. Prior to applying an exemplary nail product to a nail, it may be desirable to first treat the nail with a nail preparation (i.e., "nail prep") as is known in the art to remove oils, moisture, water, debris and/or any other substance(s) that could interfere with the adhesive nature of a later-applied tacky substance. Exemplary nail preps may comprise isopropanol, acetone and/or other similar solvents. In addition, or in the alternative, exemplary nail products may be applied to a nail that has been treated with nail primer as is known in the art.

Exemplary nail products in accordance with the present disclosure may comprise a tacky substance, fiber residue and nail coating as described in further detail below.

Figure 2:
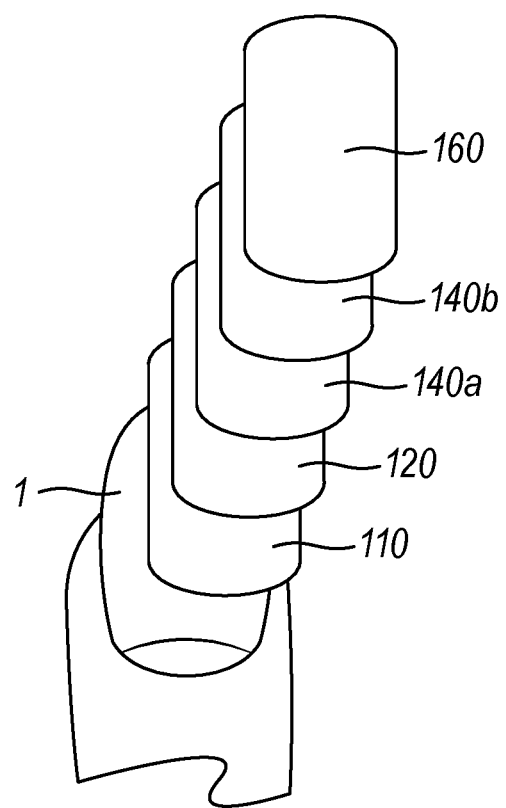
FIG. 2 depicts a graphical representation of layers of nail product applied to a nail in accordance with the present disclosure.

A useful tacky substance in accordance with the present disclosure is one that is configured to be coated on a nail and that provides sufficient bonding between keratin molecules on a nail's surface and a later-applied fiber residue, such that the fiber residue remains on the nail when a further nail coating is applied thereto. A useful tacky substance in accordance with the present disclosure may also provide sufficient bonding between two layers of nail coating, for example, when a fiber residue is deposited over a nail coating and a further nail coating is applied onto the fiber residue. Exemplary tacky substances may include nail base coats and nail adhesives that are known in the art. Useful adhesives may take any suitable form, including, but not limited to, those selected from the group of liquid adhesive, gel adhesive, hot melt adhesive and self-adhesive substrates comprising two sides, each of which comprise a full or partial adhesive coating. Exemplary synthetic adhesives of use may comprise cyanoacrylate. Exemplary natural, organic adhesives may comprise cane sugar. Referring to FIG. 2, an exemplary tacky layer (110) in the form of a base coat is applied to a nail (1).

After a tacky substance is applied to the nail, a nonwoven substrate may be applied to the nail by firmly pressing or affixing the nonwoven substrate to the nail to such that the entire nail plate, and optionally, a free-edge of the nail, is adhered to the nonwoven substrate. The nonwoven substrate is removed from the nail, leaving behind a fiber residue. In the alternative, after a tacky substance is applied to a nail, a finger or toe on which the nail is located, may be inserted into a pocket constructed from a nonwoven substrate and the outside of the pocket pressed firmly against the nail such that the entire nail plate, and optionally, a free-edge of the nail, is adhered to the nonwoven substrate. A fiber residue may comprise a random deposit of fibers that are left behind on a tacky substance disposed on a nail when the nonwoven substrate is removed from the nail. In exemplary nail products, the one or more fibers in the fiber residue, but fewer than all of the fibers in the fiber residue, may retain one or more physical and/or chemical bonds that they had with one or more further fibers when they were present in the nonwoven substrate prior to its application to the nail; these fibers may be referred to as "bonded fibers." Without wishing to be bound by theory, it is believed that the fiber residue, i.e., fibers remaining on the nail once the nonwoven substrate has been removed, provide the nail with additional tensile strength. It is further believed that the fiber residue provides additional bonding surfaces for the tacky substance and/or the later-applied nail coating to adhere. It is further believed that the fiber residue may fill or even out any nail lines, ridges, craters and/or missing portions of a nail. It is further believed that the fiber residue provide for long lasting nail coatings, in lieu of using gels or shellacs, which may require UV/UVA curing and may involve a complex removal process. It is further believed that the fiber residue may also prevent nail trauma when a later-applied nail coating (e.g., a gel or shellac) is removed from the nail. Referring to FIG. 2, a fiber residue (120) is applied to a nail (1) over tacky substance (110).

Exemplary nonwoven substrates of use to deposit a fiber residue may comprise natural fibers, synthetic fibers and combinations thereof. Exemplary fibers of use are those fibers that at least partially retain their structural integrity (i.e., do not completely dissolve) when in contact with the tacky substance and nail coating. Exemplary fibers of use may be selected from the group of monocomponent fibers, multicomponent fibers, bicomponent fibers, biconstituent fibers and combinations thereof.

Exemplary nonwoven substrates may comprise fibers selected from the group of natural fibers, synthetic fibers and combinations thereof. Sources of exemplary natural fibers may be selected from the group of silk, bamboo, hemp, jute, cotton, ramie, coir, sisal, flax, kenaf, abaca, keratin, collagen, plant based materials (e.g., green tea), herbs, purified cellulose (i.e., plant fiber) and combinations thereof. Some exemplary nonwoven substrates may comprise by weight percentage of the nonwoven substrate, at least about 95 wt %, at least about 99 wt % and as much as 100 wt % natural fibers. In other words, some exemplary nonwoven substrates are substantially free of synthetic fibers, i.e., they may contain less than about 5 wt %, less than about 1 wt %, or be completely free (i.e., contain 0%) of synthetic fibers. Exemplary synthetic fibers may comprise polymers selected from the group of polyacrylate, styrene, polyester, acrylic polymer precursors and combinations thereof. One exemplary nonwoven substrate comprises reclaimed fluff pulp that has an average fiber length of from about 1.0 to about 2.5 mm.

Figure 3:
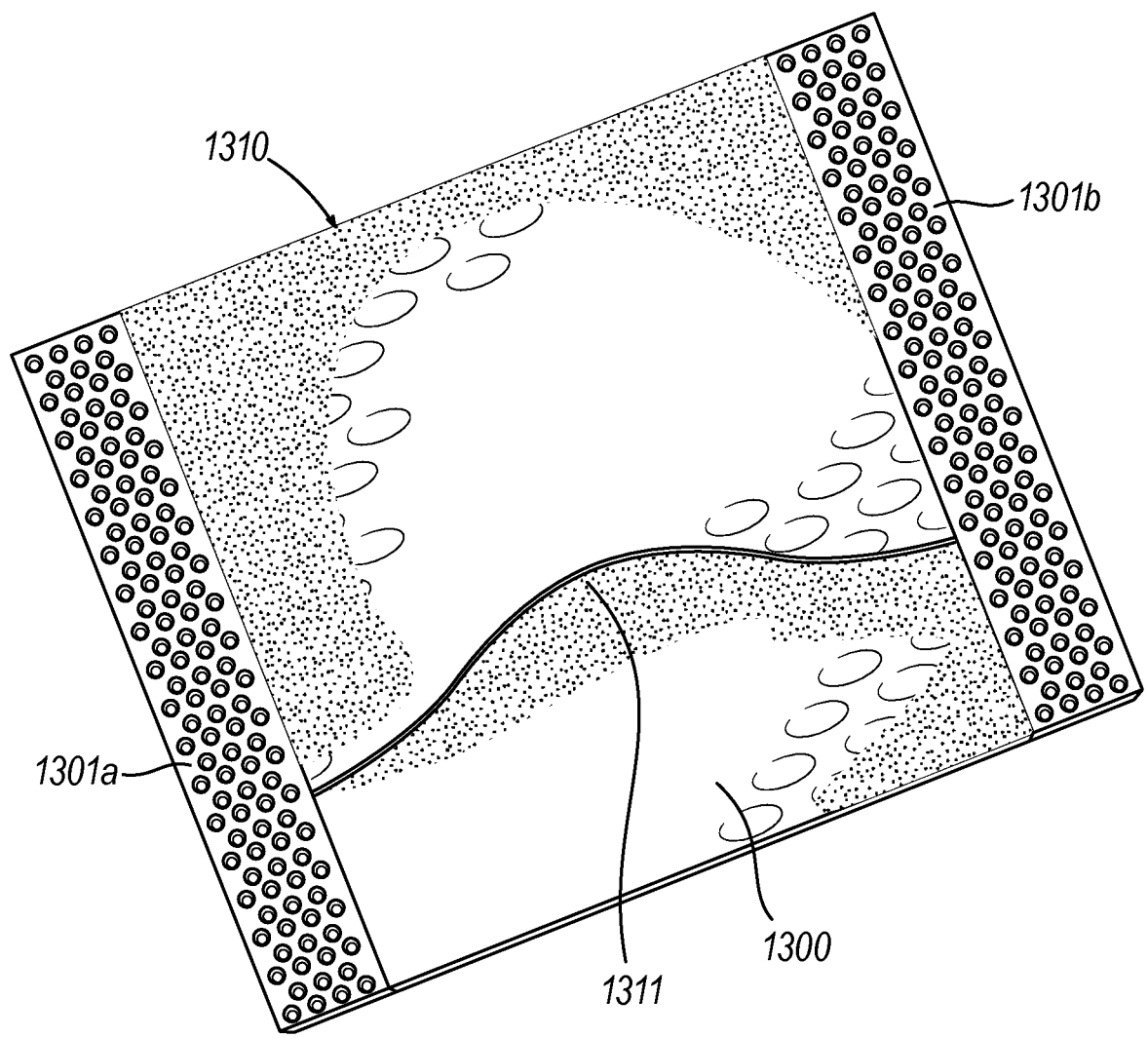
FIG. 3 depicts an exemplary nonwoven substrate in a configuration of use pursuant to the present disclosure.
Figure 4:
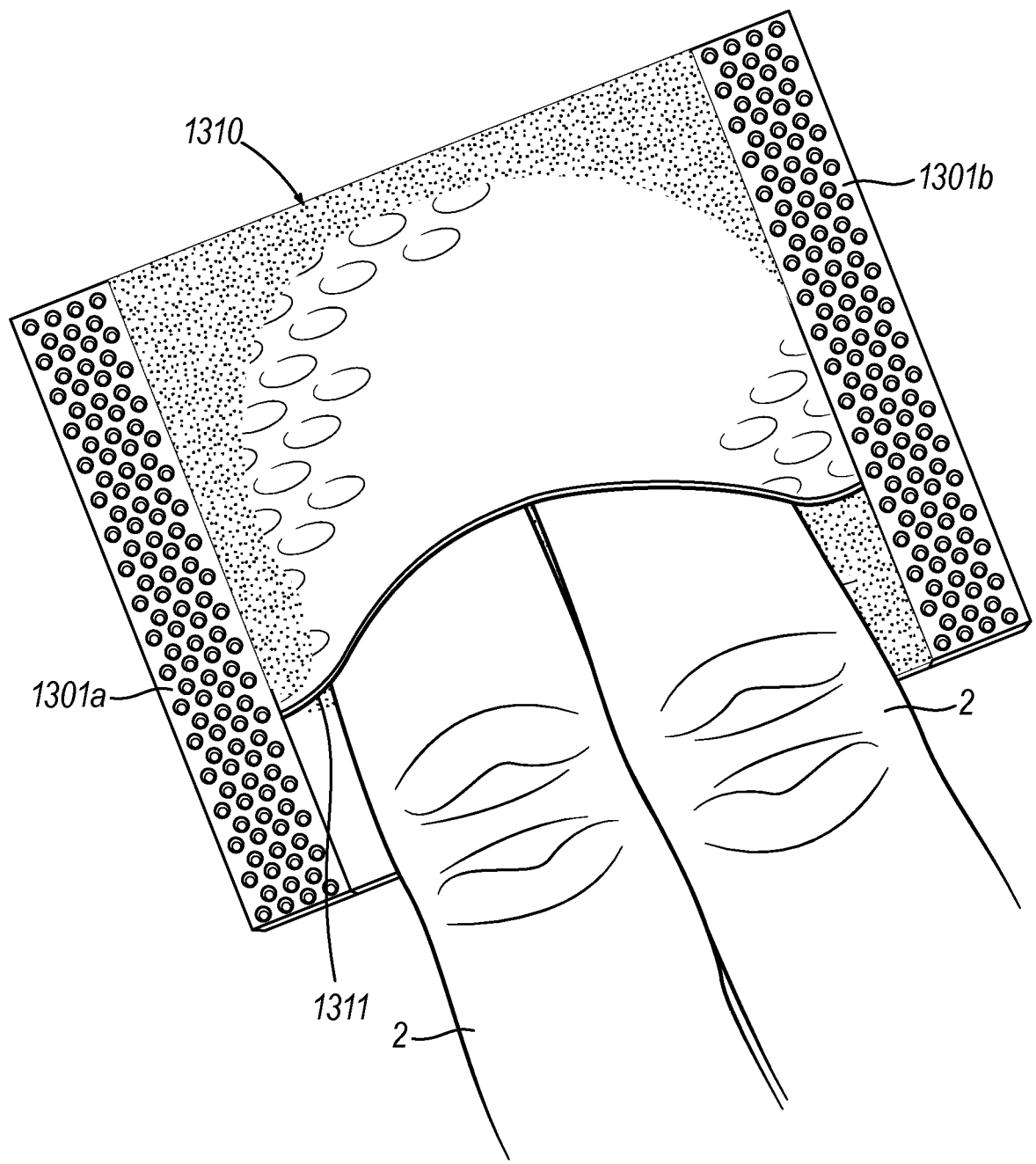
FIG. 4 depicts the exemplary nonwoven substrate in FIG. 3, with two fingers inserted therein.

Some exemplary nonwoven substrates may be substantially planar and may be cut into any desirable shape, including round or rectangular. Some exemplary nonwoven substrates may be formed into a shape that facilitates holding the nonwoven substrate during application to a nail. For example, referencing FIG. 3, a substantially planar nonwoven substrate (1300) is folded over onto itself and two overlapping edges are bonded together to form sealed edges (1301 a, b) to form a rectangular-shaped device (1310) with a pocket having one open end (1311) into which one or more fingers (2) may be inserted, as shown in FIG. 4. Wearing the rectangular-shaped pocket on the fingers of one hand facilitates applying the nonwoven substrate to nails on one's other hand, as well as applying the nonwoven substrate to the nails of another, such as a client.

Figure 5:
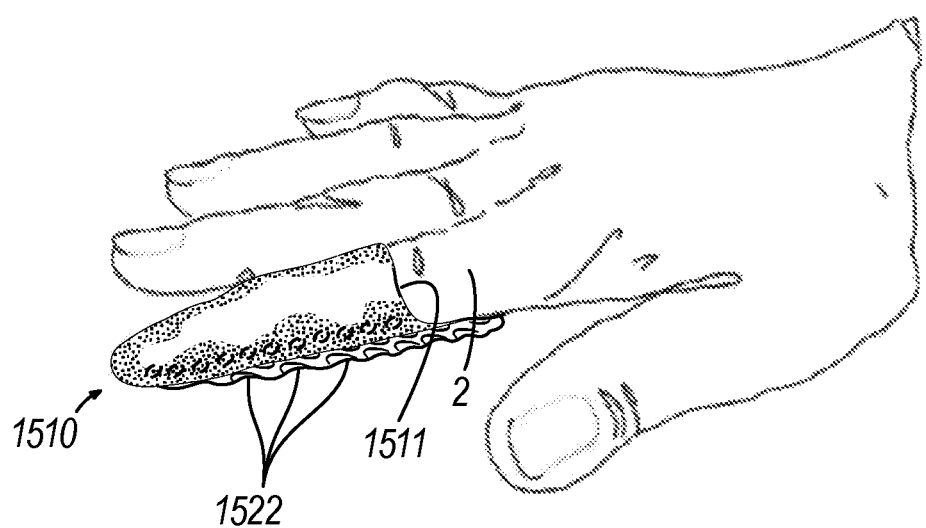
FIG. 5 depicts a further an exemplary nonwoven substrate in a further configuration of use pursuant to the present disclosure.

Referencing FIG. 5, a further exemplary nonwoven substrate is in the form of a finger glove (1510) comprising a pocket with one open end (1511) into which one finger (2) may be inserted. In this example, a fiber residue may be applied to nails on fingers that are not inserted into the finger glove (1510) and/or applied to the nail on the finger that is inserted into the finger glove (1510).

Figure 6:
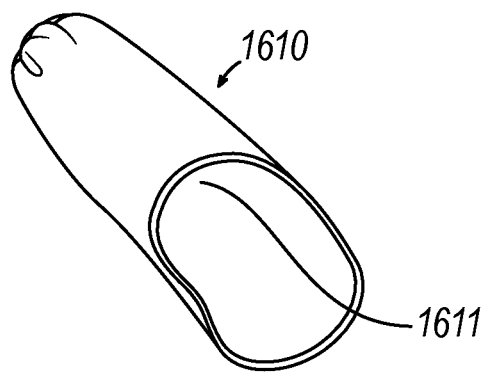
FIG. 6 depicts a further an exemplary nonwoven substrate in a further configuration of use pursuant to the present disclosure.

Referencing FIG. 6, a further exemplary nonwoven substrate in the form of a finger condom (1610) comprising a pocket with one open end (1611) into which one finger (not shown) may be inserted. In this example, a fiber residue may be applied to nails on fingers that are not inserted into the finger glove (1610) and/or applied to the nail on the finger that is inserted into the finger glove (1610).

Once fiber residue is present on the nail, loose fibers may be removed utilizing a non-grit buffer as is known in the art. Some exemplary nonwoven substrates may comprise non-grit buffer on one surface thereof. For example, referencing FIG. 5, an exemplary finger glove (1510) comprises a non-grit buffer (1522) embedded into or applied upon a portion of the finger glove (1510) for use in removing loose fibers from a nail.

Some exemplary nonwoven substrates may comprise one or more medicaments and/or nail cosmetics embedded or applied thereon (e.g., spray-coated) as is known in the art. Exemplary medicaments treat nail conditions that respond to topical treatments. Exemplary medicaments may be selected from the group of those that are anti-fungal, antibacterial and combinations thereof. Some exemplary medicaments may be used to treat or prevent a problem involving microbial growth, mostly involving fungus or bacteria development in, around, or under the artificial nail, known in the art as "greenies." Greenies is a condition which can cause onychomycosis. Some exemplary medicaments may be used to treat onychomycosis, tinea unguium and/or other nail infections as is known in the art. When these exemplary nonwoven substrates are applied to the nail, the medicaments and/or nail cosmetics may be directly transferred from the nonwoven substrate to the nail and/or deposited onto the nail along with the fiber residue, which comprises one or more fibers having the medicaments and/or conditioners applied thereto.

Some exemplary nonwoven substrates may comprise nail cosmetics selected from the group of collagen (e.g., marine collagen), sericin, plant extracts and combinations thereof. Sericin is a naturally occurring protein extracted from silk. As described in U.S. Pat. No. 6,613,339, entitled "Nail Cosmetics," sericin may make nails healthier by suppressing dryness and increasing fracture resistance, while making nails appear glossy. When such a nonwoven substrate is applied to and removed from a nail, sericin is deposited on or transferred to the nail with the fiber(s).

Some exemplary nonwoven substrates may comprise plant extracts. Exemplary plant extracts of use may be selected from the group of quebracho extract, mimosa extract and combinations thereof. As described in SE 8,400,416, entitled, "Cosmetic Compositions for Treating Human Nails Containing Quebracho and/or Mimosa Extracts," these plant extracts may be used to improve the mechanical properties of nails, in particular their toughness and resistance to knocks and breaking. Exemplary quebracho extracts of use may be selected from the group of *Schinopsis balansae* extract, *Schinopsis lorentzii* extract and combinations thereof. An exemplary mimosa of use is *Acacia mearnsii* extract.

After a fiber residue is present on a nail and any loose fibers removed if needed, a nail coating is applied to the nail. Virtually any commercially available nail coating may be used. One or more nail coatings may be applied as desired to provide for a smooth and glossy appearance. Exemplary nail coatings may be selected from the group of nail polish, nail lacquer, shellac, colored acrylic polymers (e.g., nail dip, gel polymers, silk nail wraps, etc.) and combinations thereof. Exemplary nail coatings may include those that are pigmented, clear, translucent, are matte, metallic, chromic, pearlescent, contain glitter, are in gel form and are in crème form. Referring to FIG. 2, a nail coating (140 a) is applied over fiber residue (120). If any gaps between fibers in fiber residue (120) remain after the nail coating (140 a) is applied, at least one further nail coating (140 b) is applied to provide for a smooth surface. A top coat (160) may be applied over the final nail coating applied (140 b) to provide additional shine.

Exemplary nail products as described herein may be provided (e.g., packaged) as a kit. Exemplary kits may comprise one or more of the aforementioned tacky substances, nonwoven substrates and nail coatings. Exemplary kits for home or professional use may comprise one or more containers (e.g., bottles) of base coat, one or more containers of nail polish, a plurality of finger gloves described herein as comprising a non-grit buffer disposed on a single side and one or more containers of nail polish. An exemplary kit for home use may further comprise manicuring tools and formulations selected from the group of nail prep, nail files, manicure scissors, polish remover and combinations thereof. Some exemplary kits for professional use may further comprise manicuring tools and formulations selected from the group of nail prep, nail files, manicure scissors, polish remover and combinations thereof.

Some exemplary nail products may not be packaged together as a kit, but potential users are informed (e.g. through advertisements and/or product labeling) of an associated method of use or regimen. For example, an exemplary nonwoven substrate or plurality thereof may be sold alone, for example as a kit "refill," and associated advertising and/or product labeling may inform the consumer how to use it/them in conjunction with a tacky substance (e.g., base coat) and nail coating (e.g., nail polish) as nail care regimen used to decorate nails and/or regulate the condition of nails.

Figure 7:
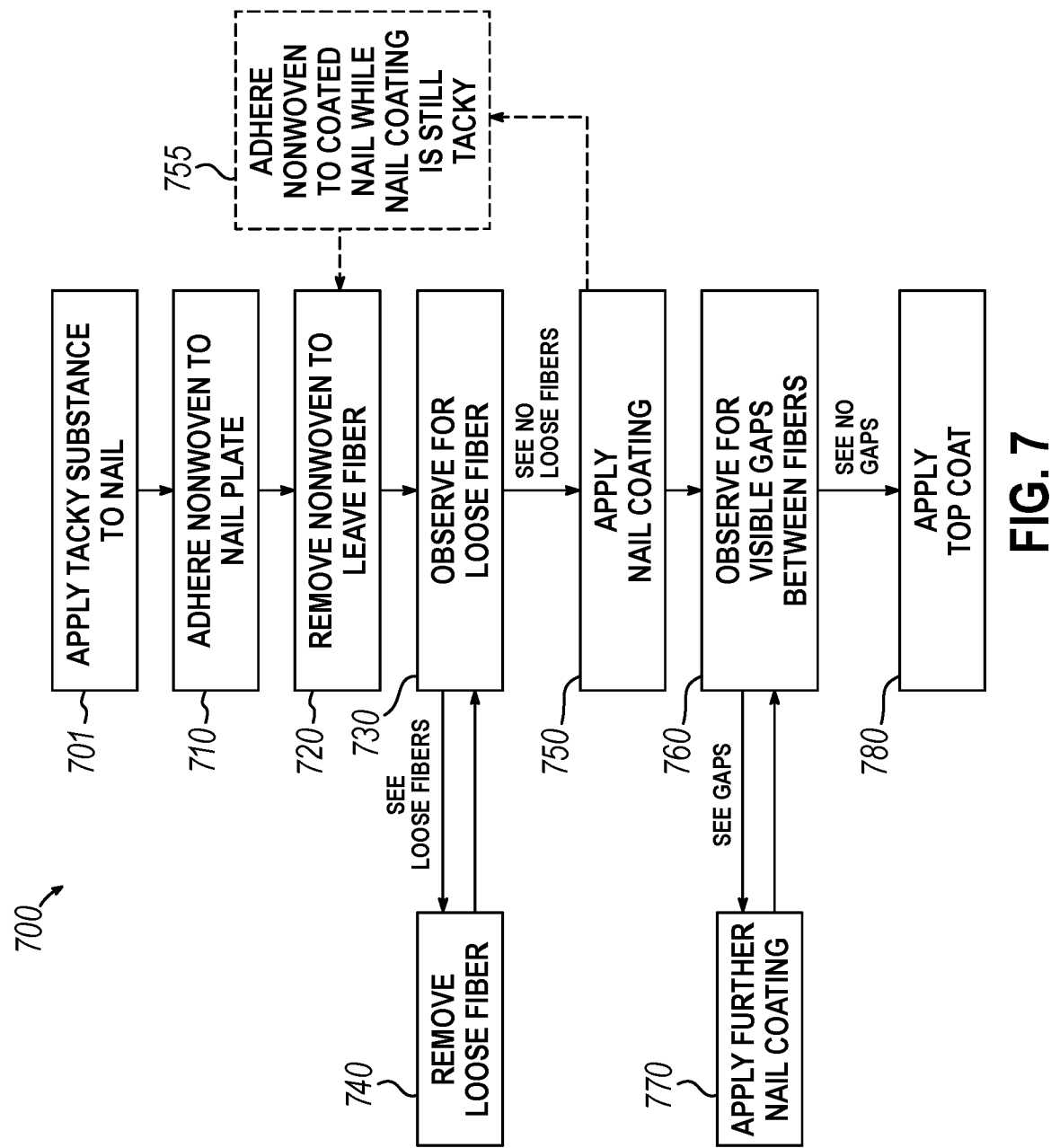
FIG. 7 depicts a flowchart showing an exemplary set of steps that may be performed to enhance a nail pursuant to the present disclosure.

FIG. 7 depicts a flowchart showing an exemplary set of steps (700) for enhancing a clean nail according to the present disclosure utilizing nail product. Drying times between steps may be observed as is known to one of skill in the art. Apply a tacky substance to the nail (block 701). Adhere a nonwoven substrate to the nail plate (block 710). Remove the nonwoven to leave a fiber residue on the nail plate (block 720). Observe fiber residue for loose fibers (block 730). If loose fibers are observed, remove loose fibers using non-grit buffer (block 740). If no loose fibers are observed, apply nail coating (block 750). Observe for gaps between fibers that are visible through the nail coating (i.e., the coating is not smooth) (block 760). If gaps are observed, apply further nail coating (block 770). If no gaps are observed, apply top coat (780). If multiple layers of fiber residue are desired, such as to further extend the life of the manicure, adhere nonwoven to coated nail before the nail coating dries (i.e., while it is still tacky) (block 755) and continue through the steps shown in blocks 720 through 780 as desired.

Figure 8:
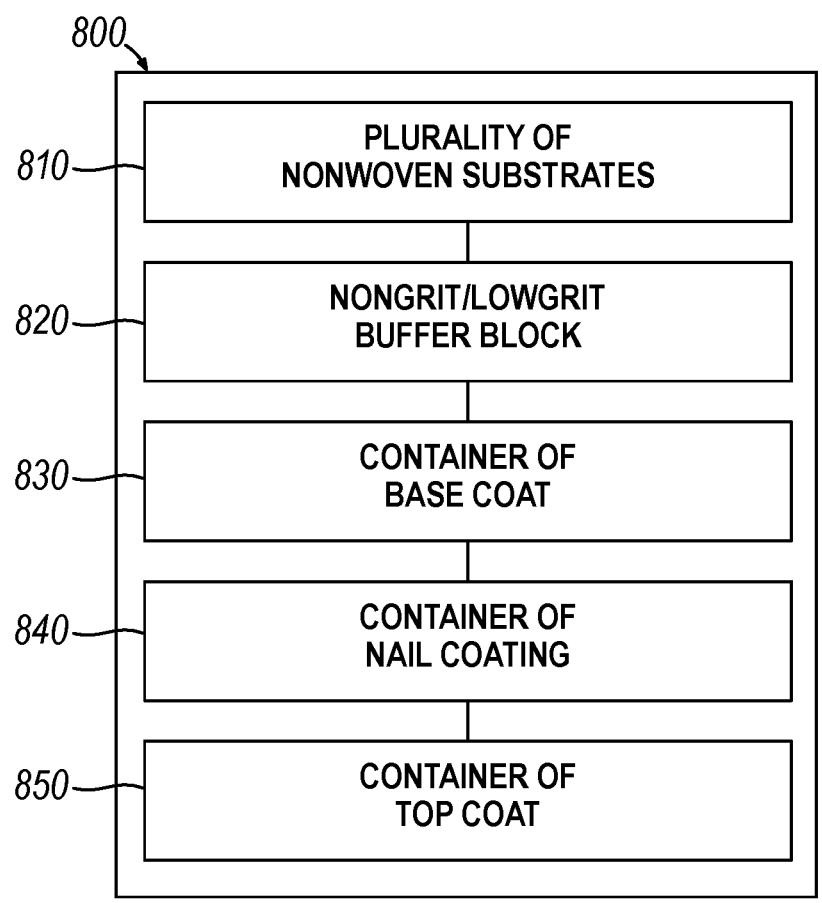
FIG. 8 depicts a graphical representation of an exemplary kit pursuant to the present disclosure.

FIG. 8 depicts an exemplary kit comprising the following that are contained within a package (800): a plurality of nonwoven substrates (810), a non-grit/low grit buffer block (820), a container (e.g., bottle) of base coat (830), a container of nail coating (840) and a container of top coat (850).

Figure 9:
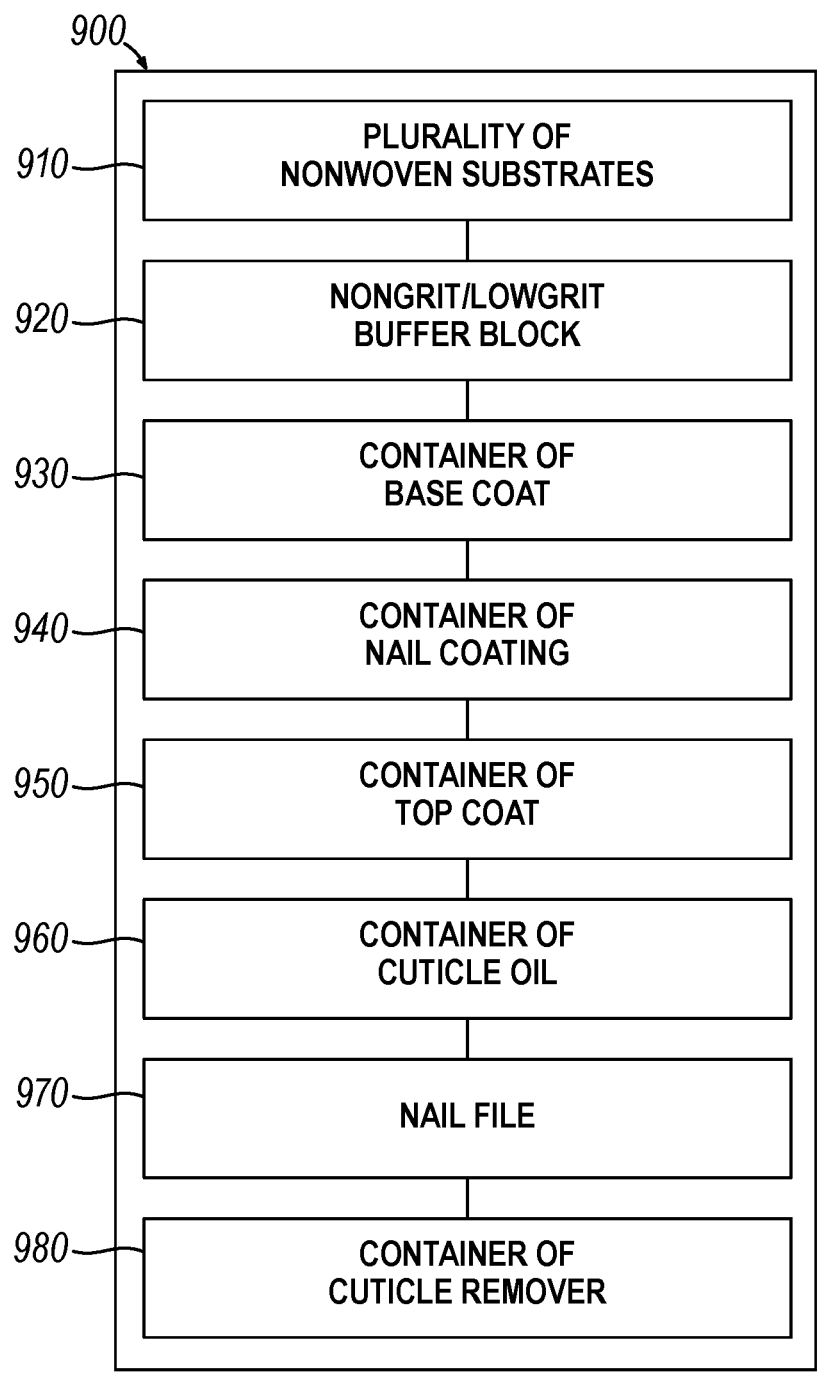
FIG. 9 depicts a graphical representation of further exemplary kit pursuant to the present disclosure.

FIG. 9 depicts another exemplary kit depicts comprising the following that are contained within a package (900): a plurality of nonwoven substrates (910), a non-grit/low grit buffer block (920), a container of base coat (930), a container of nail coating (940), a container of top coat (950), a container of cuticle oil (960), a nail file (970) and a container of cuticle remover (980).

EXAMPLES

A first exemplary method of enhancing a nail comprises: (a) applying a tacky substance to the nail; (b) supplying a nonwoven substrate having a first side and a second side disposed opposite to the first side; (c) adhering the first side of the nonwoven substrate to the tacky substance disposed on the nail; (d) removing the nonwoven material from the tacky substance, leaving a first fiber residue disposed on the tacky substance; and (e) applying a first nail coating over the first fiber residue; wherein the first nail coating adheres to the fibrous residue.

A second exemplary method for enhancing a nail according to the first exemplary method, further comprising: (a) observing the first fiber residue for loose fibers; and (b) removing any loose fibers that are observed in the first fiber residue.

A third exemplary method for enhancing a nail according the second exemplary method, wherein any loose fibers are removed using a non-grit buffer.

A fourth exemplary method of enhancing a nail according to any one of the first through third exemplary methods, wherein the second side of the nonwoven substrate comprises a non-grit buffer embedded therein or coated thereon.

A fifth exemplary method of enhancing a nail according to any one of the first through fourth exemplary methods, further comprising applying a top coat over the first nail coating.

A sixth exemplary method of enhancing a nail according to any one of the first through fifth exemplary methods, further comprising: (a) adhering a nonwoven substrate to the first nail coating while the first nail coating is still tacky, leaving a second fiber residue disposed on the first nail coating; (b) observing the second fiber residue for loose fibers; (c) removing any loose fibers that are observed in the second fiber residue; and (d) applying a second nail coating over the second fiber residue; wherein the second nail coating adheres to the second fibrous residue.

A seventh exemplary method of enhancing a nail according to the sixth method, wherein any loose fibers are removed using a non-grit buffer.

An eighth exemplary method of enhancing a nail according to the either one of the sixth and seventh methods, wherein a single nonwoven substrate is adhered to the tacky base coat on the nail and to the first nail coating on the nail while the first nail coating is still tacky.

A ninth exemplary method of enhancing a nail according to the any one of the sixth through eighth methods, wherein the nonwoven substrate comprises medicament, the method further comprising depositing the medicament onto the tacky substance disposed on the nail.

A tenth exemplary method of enhancing a nail according to the any one of the sixth through ninth methods, wherein the nonwoven substrate comprises nail cosmetic, the method further comprising depositing the nail cosmetic onto the tacky substance disposed on the nail.

An eleventh exemplary method of enhancing a nail according to the any one of the sixth through tenth methods, wherein the nonwoven substrate comprises a pocket that is configured to receive one or more fingers or toes and wherein the nail is disposed on one of the one or more fingers or toes, the method further comprising placing the one or more fingers or toes into the pocket after applying the tacky substance to the nail.

A first exemplary nail product comprising: (a) a tacky substance that is configured to be coated on a nail; (b) a nonwoven substrate that is folded over onto itself and sealed at two overlapping edges to form a pocket with one open end, wherein the nonwoven substrate is configured to: i. receive one or more fingers or toes into an interior of the nonwoven substrate through the open end of the pocket; and ii. leave a fiber residue on at least one nail disposed on at least one or more of the fingers or toes, wherein the at least one nail is coated with the tacky substance.

A second exemplary nail product according to the first exemplary nail product, wherein the nonwoven substrate is substantially free of synthetic fibers.

A third exemplary nail product according to either one of the first or second exemplary nail products, wherein the nonwoven substrate comprises medicament, nail cosmetic and combinations thereof.

A fourth exemplary nail product according to any one of the first through third exemplary nail products, wherein the medicament is selected from the group medicaments that are anti-fungal, antibacterial and combinations thereof.

A fifth exemplary nail product according to the fourth exemplary nail product, wherein the nail cosmetic is selected from the group of collagen (e.g., marine collagen), sericin, plant extracts and combinations thereof.

A sixth exemplary nail product according to any one of the first through fifth exemplary nail products, wherein the nonwoven substrate is in the form of a finger glove comprising non-grit buffer embedded into or applied upon a first exterior portion of the finger glove.

A seventh exemplary nail product according to the sixth fifth exemplary nail product, wherein the nonwoven substrate further comprises medicament, nail cosmetic and combinations thereof embedded into or applied upon a second exterior portion of the finger glove, wherein the first exterior portion of the glove and the second exterior portion of the glove do not overlap.

An eighth exemplary nail product according to any one of the first through seventh nail products, wherein the nonwoven substrate comprises reclaimed fluff pulp that having an average fiber length of from about 1.0 to about 2.5 mm.

An exemplary kit for enhancing nails, the kit comprising a package that contains (a) a plurality of nonwoven substrates; (b) a buffer block; (c) a container of base coat; (d) a container of nail coating; and (e) a container of top coat.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

I claim:

1. A nail product comprising:
   (a) a tacky substance that is configured to be coated on a nail;
   (b) a nonwoven substrate that is folded over onto itself and sealed at two overlapping edges to form a pocket with one open end; and
   (c) a fiber residue,
   wherein the nonwoven substrate is configured to:
      i) receive one or more fingers or toes into an interior of the pocket through the one open end of the pocket; and
      ii) leave the fiber residue on at least one nail disposed on at least one or more of the fingers or toes, wherein the at least one nail is coated with the tacky substance; and
   further wherein:
      1. the nonwoven substrate comprises fibers; and
      2. the fiber residue comprises fewer fibers than the nonwoven substrate.

2. The nail product of claim 1, wherein the nonwoven substrate is substantially free of synthetic fibers.

3. The nail product of claim 1, wherein the nonwoven substrate comprises a medicament, a nail cosmetic or combinations thereof.

4. The nail product of claim 3, wherein the medicament is selected from medicaments that are anti-fungal, antibacterial or combinations thereof.

5. The nail product of claim 3, wherein the nail cosmetic is selected from collagen, sericin, plant extracts or combinations thereof.

6. The nail product of claim 1, wherein the nonwoven substrate comprises reclaimed fluff pulp.

7. A nail product comprising:
   (a) a tacky substance that is configured to be coated on a nail;
   (b) a nonwoven substrate comprising fibers; and
   (c) a fiber residue comprising fewer fibers than the nonwoven substrate;
   wherein the nonwoven substrate is configured to:
      i) be applied to the tacky substance coated on the nail; and
      ii) leave the fiber residue on the tacky substance coated on the nail.

8. The nail product of claim 7, wherein the nonwoven substrate is substantially free of synthetic fibers.

9. The nail product of claim 7, wherein the nonwoven substrate comprises a medicament, a nail cosmetic or combinations thereof.

10. The nail product of claim 9, wherein the medicament is selected from medicaments that are anti-fungal, antibacterial or combinations thereof.

11. The nail product of claim 9, wherein the nail cosmetic is selected from collagen, sericin, plant extracts or combinations thereof.

12. The nail product of claim 7, wherein the nonwoven substrate comprises a first surface and a second surface, and further wherein a non-grit buffer is embedded into or applied upon the first surface of the nonwoven substrate.

13. The nail product of claim 12, wherein a medicament, a nail cosmetic or combinations thereof are embedded into or applied upon the second surface of the nonwoven substrate, wherein the first surface and the second surface of the nonwoven substrate do not overlap.

14. The nail product of claim 7, wherein the nonwoven substrate comprises reclaimed fluff pulp.

15. A kit for enhancing nails, the kit comprising one or more packages containing:
   (a) the nail product of claim 1; and
   (b) a buffer blocky.

16. A kit for enhancing nails, the kit comprising one or more packages containing:
   (a) the nail product of claim 7; and
   (b) a buffer block.

17. A method for applying the nail product of claim 1 to a nail, the method comprising:
   (a) applying the tacky substance to the nail;
   (b) inserting the nail through the one open end of the pocket and into the interior of the pocket;
   (c) while the nail is in the interior of the pocket, pressing or affixing the nonwoven substrate to the tacky substance disposed on the nail;
   (d) removing the nail from the interior of the pocket, leaving the fiber residue disposed on the tacky substance disposed on the nail; and
   (e) applying a nail coating over the fiber residue disposed on the tacky substance;
   wherein the nail coating adheres to the fiber residue disposed on the tacky sub stance.

18. A method for applying a nail product to a nail, wherein the nail product comprises:
   (a) a tacky substance;
   (b) a nonwoven substrate comprising fibers; and
   (c) a first fiber residue comprising fewer fibers than the nonwoven substrate;
   the method comprising:
      i) applying the tacky substance to the nail;
      ii) pressing or affixing the nonwoven substrate to the tacky substance applied to the nail;
      iii) removing from the nail the nonwoven substrate that has been pressed or affixed to the nail, leaving a first fiber residue on the tacky substance; and
      iv) applying a first nail coating over the first fiber residue on the tacky sub stance.

19. The method of claim 18, further comprising applying a second nail coating over the first nail coating.

20. The method of claim 18, further comprising:
   v) pressing or affixing a nonwoven substrate to the first nail coating while the first nail coating is still tacky;
   vi) leaving a second fiber residue disposed on the first nail coating; and
   vii) applying a second nail coating over the second fiber residue;

wherein the nonwoven substrate of step v) is the same or different from the nonwoven substrate of step ii).

* * * * *